United States Patent [19]

Rohbock et al.

[11] 4,111,832

[45] Sep. 5, 1978

[54] PROCESS FOR REGENERATING SPENT VANADIUM OXIDE CONTAINING OXIDATION CATALYSTS

[75] Inventors: Klaus Rohbock, Krefeld; Rudolf Wiemers, Meerbusch; Peter Woditsch; Reinhard Thiel, both of Krefeld, all of Germany

[73] Assignee: Bayer Aktiengesellschaft, Leverkusen, Germany

[21] Appl. No.: 743,725

[22] Filed: Nov. 22, 1976

[30] Foreign Application Priority Data

Nov. 22, 1975 [DE] Fed. Rep. of Germany ....... 2552456

[51] Int. Cl.$^2$ .................... B01J 23/94; B01J 23/92; B01J 27/28
[52] U.S. Cl. ..................... 252/412; 260/346.4; 260/346.75; 260/604 R; 562/547; 562/549; 562/542

[58] Field of Search .............. 252/412, 414; 423/68; 260/346.8 A, 346.75, 346.4

[56] References Cited

U.S. PATENT DOCUMENTS

| 2,298,091 | 10/1942 | Cooper, Jr. et al. | 423/68 |
| 3,168,481 | 2/1965 | Erickson | 252/412 |
| 3,538,017 | 11/1970 | Aglietti et al. | 252/412 |

*Primary Examiner*—P. E. Konopka
*Attorney, Agent, or Firm*—Burgess, Dinklage & Sprung

[57] ABSTRACT

A process for regenerating a deactivated oxidation catalyst, especially one containing vanadium oxide, wherein the deactivated catalyst is treated with an aqueous solution of ammonia and/or an amine at an elevated temperature so as to dissolve at least a portion of the catalyst and the resultant solution or suspension is treated in a known manner to obtain the reactivated catalyst.

10 Claims, No Drawings

PROCESS FOR REGENERATING SPENT VANADIUM OXIDE CONTAINING OXIDATION CATALYSTS

BACKGROUND OF THE INVENTION

1. Field of Invention

The invention relates to a process for regenerating oxidation catalysts containing vanadium oxide.

It is known that complex catalysts containing vanadium oxide, which are used, for example, for the production of maleic anhydride by catalytic oxidation of butane with molecular oxygen, become deactivated with time. A process for reactivating these deactivated catalysts, by treatment with a reducing agent, is also known (German Offenlegungsschrift (Published Specification) 2,353,136). However, the recovered activity and selectivity of the catalyst does not last long, so that the reductive treatment must be repeated after only a relatively short time.

It is also known to convert the vanadium pentoxide, of the spent catalysts, into volatile vanadium oxychloride by treatment with thionyl chloride or phosgene, and to convert this compound into vanadium pentoxide in the usual manner. In an even better way, vanadium pentoxide may be recovered from catalysts which contain vanadium pentoxide by treating the catalysts with carbon tetrachloride at not less than 100° C. and reacting the volatile reaction mixture with ammonia to give ammonium vanadate (German Offenlegungsschrift (Published Specification) 2,228,927). In these processes, the catalyst is not actually regenerated and instead only vanadium is selectively recovered, and at the same time auxiliary materials are consumed and problems of recovery or disposal both of the by-products resulting therefrom, and of the residual constituents of the catalyst, arise.

Accordingly, there is lacking a process which permits the regeneration of such catalysts in a technically simple manner. In this context, regeneration is generally understood as a process which makes it possible to obtain an active catalyst from a deactivated catalyst.

SUMMARY OF THE INVENTION

Broadly, this invention contemplates a process for regenerating a deactivated oxidation catalyst, especially a deactivated vanadium oxide oxidation catalyst, which comprises contacting the deactivated catalyst with an aqueous solution of ammonia and/or an amine at an elevated temperature whereby to at least partially dissolve the catalyst, optionally separating the resultant solution or suspension from undissolved catalyst and/or support material and treating the resultant solution or suspension in a known manner to obtain the catalyst.

It has now been found that deactivated oxidation catalysts containing vanadium oxide can be regenerated by a process wherein (a) the deactivated catalyst is treated with an aqueous solution of ammonia and/or an amine at an elevated temperature, so that the catalytically effective constituents of the catalyst are partially or completely dissolved, (b) water and ammonia and/or amine are removed completely or partially from the resulting solution and/or suspension, (c) after filtering off, if appropriate, undissolved catalyst and/or support material, and (d) the mass thus obtained is reprocessed in a known manner to give the catalyst, if appropriate with addition of support material.

The process according to the invention is suitable, for example, for regenerating a catalyst containing salts especially alkali salts, e.g. sodium salts and/or oxides of vanadium, molybdenum, titanium and/or manganese and which are applicated, if appropriate, on a porous support (e.g. German Patent Specification No. 1,267,205).

Preferably, the process according to the invention is suitable, for example, for regenerating complex phosphorusvanadium-oxygen catalysts, such as are described, for example, in the abovementioned Offenlegungsschriften (German Published Specifications) or U.S. Pat. No. 3,625,863 and British Pat. No. 1,235,424. These catalysts may contain, in addition to vanadium and phosphorus, also other elements as promoters, such as, for example, copper, cadmium, zinc, nickel, cobalt and either only one or several of these elements; further useful promoters of this type are silver, thallium, tungsten, aluminum, tin, manganese, bismuth, iron, selenium, sodium, lithium, calcium, strontium and niobium.

The catalysts containing vanadium oxide mentioned above are of considerable industrial importance as oxidation catalysts and are used, for example, for the oxidative preparation of phthalic anhydride from naphthalene or o-xylene, of maleic acid from benzene, of maleic acid and acetic acid from $C_4$-hydrocarbons and of methacrolein from isobutene and of acrylic acid from propene.

The process according to the invention can be employed both for the regeneration of unsupported catalysts and of supported catalysts.

Useful supports for the supported catalysts containing vanadium oxide are the usual catalyst supports, such as aluminum oxide, silicon dioxide, titanium dioxide, silicon carbide, silicas, pumice, kieselguhr, corundum, alumina, quartz and porcelain.

Amines which can be used for the process according to the invention are practically all amines which, as such or as quaternary ammonium salts, are soluble in water (compare H. Beier, Lehrbuch der organischen Chemie (Textbook of Organic Chemistry), 11th/12th edition, pages 123, 482 and 604 (1966)).

Advantageously, commercially available amines of the formula

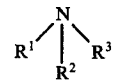

in which $R^1$, $R^2$ and $R^3$ are identical or different and represent hydrogen or aliphatic, cycloaliphatic, araliphatic or aromatic radicals, are used.

Examples of aliphatic radicals which may be mentioned are straight-chain or branched alkyl radicals with up to 10, preferably up to 5, carbon atoms.

Cycloaliphatic radicals which may be mentioned are those with up to 10 carbon atoms, preferably cyclopentyl and cyclohexyl.

Araliphatic radicals which may be mentioned are those with up to 10 carbon atoms, preferably phenylalkyl radicals with up to 4 carbon atoms in the chain, and especially benzyl.

Aromatic radicals which may be mentioned are those with 6 and 10 ring carbon atoms, especially phenyl and naphthyl, and these radicals can optionally also be substituted by hydrocarbon radicals, especially by lower alkyl radicals.

Accordingly, primary, secondary or tertiary aliphatic, cycloaliphatic, araliphatic and aromatic amines can be used in the process according to the invention.

For example, monomethylamine, dimethylamine and trimethylamine, monoethylamine, diethylamine and triethylamine, monopropylamine, dipropylamine and tripropylamine, monobutylamine, dibutylamine and tributylamine, monooctylamine, dioctylamine and trioctylamine and tert.-butylamine may be mentioned as aliphatic amines.

Further, benzylamine, aniline and diphenylamine may be mentioned as examples of araliphatic and aromatic amines.

However, mixed aliphatic-aromatic amines may also be used, for example N,N-dimethylaniline.

Furthermore, cyclic amines can also be used, and in particular both aromatic and non-aromatic amines; pyridine and piperidine may be mentioned as examples.

In general it is advantageous to grind the deactivated catalyst prior to the treatment with the aqueous solution but this is not absolutely essential. In general, the deactivated catalyst is ground to a particle size of 40 to 1,000μ, preferably 60 to 500μ, but larger and smaller particles may also still be present. It may be advantageous to grind the catalyst to as small a particle size as possible in order to achieve more rapid solution of the catalyst.

Even when regenerating supported catalysts it is in general advantageous to grind the deactivated catalyst as described above.

However, this does not apply if the deactivated catalyst is a catalyst of the layer- or shell-type; in that case, grinding is advantageously omitted.

In general, the treatment of the deactivated catalyst is carried out with the aqueous ammonia and/or amine solution at an elevated temperature in the range from 100° to 250° C., preferably 130° to 180° C.

Inherently, the process according to the invention can be carried out under normal pressure, for example by heating with the aqueous solution under reflux.

However, in general it is advantageous to work under elevated pressures preferably up to 300 bars, in a closed pressure vessel. This is particularly advantageous if ammonia or an amine is used which boils at a lower temperature than water. In that case, the process can be carried out at the vapor pressure corresponding to the temperature of the aqueous solution, and in the preferred temperature range of 130° to 180° C. a pressure of about 5 to 50 bars results which, as is known, depends on the concentration of the aqueous solution and the nature of the amine.

One can also work at a higher pressure than the vapour pressure corresponding to the selected temperature, for example when using low-boiling amines, by setting up the desired higher pressure by injecting ammonia or a readily volatile amine or an inert gas.

In general it is advantageous if the deactivated catalyst or at least its catalytically effective constituents dissolve as completely as possible during the treatment with the aqueous solution of ammonia and/or amines; however, complete solution is not absolutely essential.

In this context, catalytically effective constituents of the catalyst are understood as its active constituents without its inert support material which are fully desactivated or may be further active to some degree.

A degree of solution of 25% can already suffice; in this context, degree of solution is understood as the ratio of the dissolved weight, to the weight employed, of the deactivated catalyst, without support material.

In general it is, however, advantageous to achieve as high a degree of solution as possible. The amount and concentration of the aqueous solution appropriate for this purpose depends in general on the nature of the amine used and on the composition of the vanadium oxide containing catalyst which is to be regenerated. It can, in each individual case, be determined easily by a few preliminary experiments.

In general, aqueous ammonia solutions containing from 5 to 32, especially from 15 to 30, percent by weight of $NH_3$, preferably commercially available solutions containing 27 percent by weight $NH_3$, are used in an amount of 1 to 20, preferably 3 to 10, milliliters per gram of deactivated catalyst.

Aqueous solutions of amines are in general used in an amount of 2 to 50, preferably of 5 to 25, milliliters per gram of deactivated catalyst; their concentration is in general 0.2 to 3.0, preferably 0.5 to 2.0, mols per liter of water. Preferably, aqueous solutions of the amines are used which are saturated at room temperature.

It can however also be advantageous to use mixtures of water and amine in such concentrations as correspond to the concentrations of saturated solutions at the reaction temperature. Suitably, however, mixtures of water and amine in such amounts should be used that the amount of the amine corresponds at least to the stoichiometric amount which is required to form ammonium salts and/or amine complexes of those catalyst constituents which can be converted into these types of compounds, for example ammonium vanadate, ammonium molybdate, ammonium tungstate, ammonium phosphate, copper tetramine complexes, and zinc amine complexes.

In general, any amount of the ammonia and amine solution may be used, but for economic reasons the excess beyond the minimum amount required will be kept as low as possible, since water and ammonia and/or amine must be removed, by evaporation, in the second stage of the process according to the invention.

The process according to the invention is simple to carry out. The deactivated catalyst, which has been ground if appropriate, can be heated, for example in a stirred kettle, under reflux, with the amine solution being used, until the desired degree of solution is reached. It is, however, also possible to treat the deactivated catalyst, which has been ground if appropriate, in a stirred autoclave with the aqueous ammonia and/or amine solution, under autogenous pressure or optionally, as mentioned above, under a higher pressure, until the desired degree of solution is reached.

This first step of the process is new and essential to regenerate a deactivated catalyst. The following steps of treating the obtained solution or suspension can be carried out in the usual manner to prepare a catalyst from a solution of suspension of its constituents. The steps to prepare a catalyst from a solution or suspension of its constituents are known in the art.

The solution can be evaporated and the catalyst can be prepared by further drying and forming, if appropriate after grinding. It may be further calcinated before or after forming. Support material may be added either to the solution or to the residue after evaporation. Furthermore to obtain a impregnated catalyst the support can be impregnated with the solution and further processed as known in the art. Further, to obtain a layer- or shell-type catalyst the pasty residue of the evaporated solution can be applied to the support as known in the art.

The solution or suspension obtained by treating the deactivated catalyst with the aqueous solution of ammonia and/or amine can subsequently be evaporated in the usual manner, for example by evaporating under normal pressure or reduced pressure, to a pasty consistency or to dryness, and the mass thus obtained can be further treated for the forming of the regenerated catalyst in a known manner.

As already explained, complete solution of the deactivated catalyst is not necessary and hence the undissolved part does not have to be separated off and the entire suspension can be used as described above.

However, it is also possible to separate off the undissolved constituent, for example by filtration, from a suspension which is obtained, and use only the filtrate for the preparation of regenerated catalyst.

When regenerating a supported catalyst, the conditions are different inasmuch as the undissolved part consists mainly of support material. Hence, to prepare a regenerated catalyst of the same composition, the conjoint use of the undissolved constituent is inherently necessary. However, also in this case it is possible to filter off the undissolved constituent, which can consist either only of support material or of support material and undissolved supported catalyst, and to add an appropriate amount of support material, in a known manner, either to the filtrate or at a later stage of the preparation to the regenerated catalyst.

On the other hand, when regenerating a catalyst of the layer- or shell-type it can be advantageous to carry out the working up of the solution obtained, by separating off the solution from the undissolved support. The catalyst of the layer-or shell-type can then be prepared from the separated catalyst support and catalyst solution in a known manner, if appropriate after prior concentration of the solution. In this case it can furthermore be advantageous to use new molded supports instead of the original catalyst supports, especially if not only the catalyst was deactivated but also the molded supports were damaged.

As already explained, the process according to the invention can be employed, for example, for regenerating fixed bed oxidation catalysts which have been prepared in accordance with the process of U.S. Pat. No. 3,625,863.

According to this special variant of the process according to the invention, the entire solution or suspension obtained by treating the deactivated catalyst with an aqueous solution of ammonia and/or amines is evaporated, the resulting composition is dried in accordance with the process of the above lastmentioned U.S.-patent and calcined in the presence of air at temperatures between about 300° and about 650° C., and the calcined product is then ground and finally molded without using higher temperatures.

Of course, the vapor mixture of water and ammonia and/or amines, obtained in step (b) of the process according to the invention, i.e. the evaporation process, can be condensed in the usual manner, and water, ammonia and/or amine can be recovered. In this process, either separation into the individual components can already be achieved by fractional condensation, or the condensate can subsequently be separated, for example by fractional distillation. Furthermore, it is possible, and can be advantageous, to use the resulting condensate subsequently, as such or if appropriate after addition of water, ammonia or amine, for the treatment of a further batch of the deactivated catalyst.

In every case, one advantage of the process according to the invention results merely from the fact that the auxiliaries used, and their excess, can substantially be recovered in a very simple manner and can, if appropriate, also be separated from one another in an equally simple manner.

The essential technical progress, i.e. the possibility of regenerating and reusing deactivated catalyst, is the process according to the invention in itself.

However, further advantages stem therefrom, such as the saving of material for the preparation of new catalysts which would otherwise be necessary, as well as the saving of the cost involved in recovery of individual constituents of the deactivated catalyst, or in the dumping of the catalyst. This is at the same time associated with the elimination of any pollution of the environment. The process according to the invention is thus particularly advantageous from an environmental point of view.

The catalysts prepared according to the process of the invention have virtually the same properties as those of newly prepared catalysts, or those which the deactivated catalysts possessed originally.

EXAMPLE 1

(a) A catalyst of which the composition by weight is $V_2O_5 : P_2O_5 : CuO = 1 : 1.5 : 0.3$ was prepared in accordance with the process of U.S. Pat. No. 3,625,863 from a solution of 1,250 g of 85 percent strength by weight phosphoric acid (remainder water) in 2,100 ml of water, 686 g of ammonium vanadate and 800 g of copper acetate in 600 ml of water, and 3,000 ml of 25% strength ammonia, and was employed for the oxidation of a butane-butene mixture with atmospheric oxygen.

The single reaction tube of the reactor used had a diameter of 25 mm and a length of 3 m and was surrounded by an electrically heated salt melt. The tube was filled with the loose catalyst to a height of 260 cm.

Per liter of catalyst, 3.6 Nm$^3$/hour of air, charged with 38 g/Nm$^3$ of a C$_4$-mixture which consisted to the extent of about 80% of n-butenes, were passed through. The reaction temperature was 420° C.

85 percent by weight, relative to the butene employed, of maleic anhydride were thus obtained.

After continuous operation for several years, the yield had fallen to 71 percent by weight of maleic anhydride, relative to butene employed.

(b) 1,000 g of this deactivated catalyst were ground and treated with 10 l of 27% strength ammonia solution in a 20 liter stirred autoclave for 5 hours at about 150° C. and a pressure of 25 bars. This resulted in 95% solution of the deactivated catalyst (degree of solution 95%).

The suspension thus obtained was subsequently evaporated at 150° C. in a rotary evaporator until a firm paste formed.

This paste was subsequently dried for 4 hours at about 210° C.

The dried product was then heated from 200° C. to 450° C., raising the temperature about 10° C. per hour, in the presence of oxygen, and the temperature of about 450° C. was then maintained for a further 16 hours.

The material was then ground to a particle size of 40 to 500μ and pressed, with addition of 2 percent by weight of aluminium stearate as a binder, to give 6 mm spheres.

(c) The regenerated catalyst obtained according to (b) was then used in the apparatus described under (a) for the oxidation of the C$_4$-mixture. The yield of maleic anhydride, relative to the butene employed, was again 85 percent by weight. Even after 1,500 operating hours the average yield was still 84 percent by weight of maleic anhydride, relative to the butene employed, and showed no greater decrease than is also observed with a catalyst which has directly been prepared new.

EXAMPLES 2 TO 6

(a) In these examples, the deactivated catalyst described in Example 1(a) was used. 2,000 g portions of the ground deactivated catalyst were treated, in the amount of 27 percent strength by weight aqueous ammonia solution indicated in Table I, at the temperatures and pressures, and for the reaction times, which are also indicated in Table I.

After completion of the reaction, the amount of undissolved residue, and hence the degree of solution achieved, was determined by filtering an aliquot portion, washing the residue with aqueous ammonia and drying to constant weight at 120° C.

(b) The remaining part of the suspensions obtained according to (a) was further processed in accordance with Example 1(b) and the catalysts thus obtained were employed, as described in Example 1(c), for periods of 500 hours for the oxidation of butene to maleic anhydride. The last column of Table I shows the yield of maleic anhydride, relative to butene employed. In no case was a decrease in catalyst activity and catalyst selectivity, that is to say a decrease in the yield of maleic anhydride, observed during the operating time of 500 hours.

Table I

| Example | NH$_3$ solution, l | Reaction temperature, °C | Pressure bars | Time hours | Degree of solution achieved | Yield of maleic anhydride, % by weight |
|---|---|---|---|---|---|---|
| 2 | 20 | 100 | 1 | 3 | 25 | 81 |
| 3 | 20 | 120 | 13.5 | 6 | 87 | 84 |
| 4 | 20 | 150 | 23.5 | 6 | 98 | 85 |
| 5 | 20 | 150 | 23.0 | 1 | 92 | 85 |
| 6 | 5 | 150 | 16.0 | 6 | 96 | 85 |

EXAMPLE 7

(a) 500 g of unground catalyst spheres of the deactivated catalyst from Example 1(a) were treated with 2.5 l of 27 percent strength by weight aqueous ammonia solution in a stirred autoclave at 150° C. and a pressure of 25 bars for 5 hours.

In the course thereof, 88 percent by weight of the deactivated catalyst were brought into solution. The resulting suspension was filtered and the filtrate was processed analogously to Example 1(b), to give the regenerated catalyst.

(b) When using the catalyst regenerated according to (a) for the oxidation of butene to maleic anhydride, as described in Example 1(c), the yield of maleic anhydride was 85 percent by weight, relative to butene employed.

EXAMPLE 8

(a) 1,000 g of the deactivated catalyst described in Example 1(a) were ground and treated with 10 l of 30 percent strength by weight aqueous dimethylamine solution in an autoclave at 150° C. and a pressure of 22 bars. In the course thereof, 79 percent by weight of the catalyst were dissolved (degree of solution 79%).

(b) The suspension thus obtained was processed further as described in Example 1(b) and the regenerated catalyst thus obtained was used, as described in Example 1(c), for the oxidation of butene to maleic anhydride. The yield of maleic anhydride, relative to butene, was 84%.

EXAMPLE 9

(a) 1,000 g of the deactivated catalyst described in Example 1(a) were ground and filled, together with 2.5 l of 27 percent strength by weight aqueous ammonia solution, into a stirred autoclave. Before heating up, a pressure of 8.5 bars was set up in the autoclave by injecting ammonia gas. After heating up to 150° C., the pressure in the autoclave was 16 bars. After a reaction time of 6 hours at 150° C., 97 percent by weight of the deactivated catalyst had dissolved (degree of solution 97%).

(b) The suspension thus obtained was processed as described in Example 1(b) to give the regenerated catalyst. This regenerated catalyst, used in the oxidation of butene as described in Example 1(c), gave a yield of 85 percent by weight of maleic anhydride, relative to butene.

EXAMPLE 10

(a) A catalyst with zinc as the promoter was prepared in accordance with Example I, B of U.S. Pat. No. 3,862,146 and was then employed for oxidising a butane-butene mixture with atmospheric oxygen.

In this, the procedure described in Example 1(a) was followed. 79 percent by weight of maleic anhydride, relative to butene employed, were obtained; after several months' continuous operation, the yield had, however, fallen to 72 percent by weight of maleic anhydride, relative to butene employed.

(b) 1,000 g of this deactivated catalyst were ground and treated with 8 l of 27 percent strength by weight ammonia solution in a 20 l stirred autoclave for 6 hours at 150° C. and a pressure of 25 bars. 92 percent by weight of the deactivated catalyst were thereby brought into solution (degree of solution 92%).

(c) The suspension thus obtained was processed as described in Example 1(b) to give catalyst mouldings, which were reused in the apparatus described in Example 1(a). The yield of maleic anhydride, relative to butene employed, was 79 percent by weight. Here again, in continuous operation, the decrease observed was no greater than in the case of the catalyst freshly prepared from the starting materials.

EXAMPLE 11

(a) A catalyst for the oxidation of aromatic hydrocarbons consisting of 26,2% by weight of TiO$_2$, 16.4% by weight of NaVO$_3$, 57,4% by weight of sea sand was prepared in accordance with Example 3(b) of German Patent No. 1,267,205. It was tested for several months in continuous operation in the apparatus described in Example 1(a).

The throughput was 1.7 Nm$^3$ of air per liter of catalyst per hour, the charge was 38 g of naphthalene per Nm$^3$ of air and the salt bath temperature was 385° C.

The yield of crude phthalic anhydride was initially 88 percent by weight; after about 8 months it had fallen to 81 percent by weight, in each case relative to naphthalene employed.

(b) 1,000 g of this deactivated catalyst were comminuted and treated with 6 l of 30 percent strength by weight ammonia solution in a 20 l stirred autoclave for 5½ hours at 150° C. and a pressure of 25 bars. After this time, 16 percent by weight of the catalyst had dissolved; the insoluble residue of titanium dioxide and sea sand was filtered off.

The solution obtained was evaporated in a rotary evaporator until a highly viscous mass was formed, and was used to prepare a reactivated catalyst, with addition of finely granular anatase and of sea sand purified by treatment with HCl, in accordance with Example 3(b) of the German Patent Specification mentioned.

On renewed use of the catalyst for the oxidation of naphthalene as described under (a), 88 percent by weight of phthalic anhydride, relative to naphthalene employed, were obtained.

What is claimed is:

1. A process for regenerating a deactivated $V_2O_5$: $P_2O_5$: CuO hydrocarbon oxidation catalyst which comprises contacting the deactivated oxidation catalyst with a solution consisting essentially of an aqueous solution of ammonia and/or an amine at a temperature of from 100° to 250° C., whereby to dissolve at least partially the catalytically effective constituents of of the catalyst, drying the resultant solution or suspension and calcining the same at temperatures between 300° and 650° C. in the presence of air, grinding the resultant solid and thereafter molding the same into a final catalyst form.

2. A process according to claim 1 wherein an aqueous ammonia solution is employed and the ammonia solution contains from 5 to 32 percent by weight of ammonia.

3. A process according to claim 2 in which an aqueous ammonia solution is employed and the ammonia solution contains 15 to 30 percent by weight of ammonia.

4. A process according to claim 1 wherein the temperature is from 130° to 180° C.

5. A process according to claim 1 wherein the process is carried out at a pressure up to 300 bars.

6. A process according to claim 5 wherein the process is carried out at a pressure of 5 to 50 bars.

7. A process according to claim 1 wherein an amine is used which amine has the formula

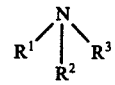

wherein
$R^1$, $R^2$ and $R^3$ are independently selected from the group consisting of hydrogen, aliphatic, cycloaliphatic, araliphatic and aromatic radicals.

8. A process according to claim 7 wherein the aliphatic radical is a straight chain or branched alkyl radical having up to 10 carbon atoms, the cycloaliphatic radical is one having up to 10 carbon atoms, the araliphatic radical is one having up to 10 carbon atoms in which the aryl portion is phenyl and the aliphatic portion is alkyl having up to 4 carbon atoms in the chain and the aromatic radical is one having betweemn 6 and 10 ring carbon atoms.

9. A process according to claim 1 wherein an amine is employed said amine being selected from the group consisting of monomethylamine, dimethylamine, trimethylamine, monoethylamine, diethylamine, triethylamine, monopropylamine, dipropylamine, tripropylamine, monobutylamine, dibutylamine, tributylamine, monooctylamine, dioctylamine, trioctylamine, tert.-butylamine, benzylamine, aniline, diphenylamine, N,N,-dimethylaniline, pyridine and piperidine.

10. A process according to claim 1 wherein an aqueous solution of dimethylamine is employed.

* * * * *